United States Patent [19]

Baum et al.

[11] Patent Number: 5,017,734

[45] Date of Patent: May 21, 1991

[54] ETHYNYL ADAMANTANE DERIVATIVES AND METHODS OF POLYMERIZATION THEREOF

[76] Inventors: Kurt Baum, 3755 Canfield Rd., Pasadena, Calif. 91107; Thomas G. Archibald, 210 N. Arden Blvd., Los Angeles, Calif. 90004; Aslam A. Malik, 708 N. Bradish Ave., Sam Dimas, Calif. 91773

[21] Appl. No.: 448,349

[22] Filed: Dec. 11, 1989

[51] Int. Cl.$^5$ .......................................... C07C 13/615
[52] U.S. Cl. ..................................... 585/21; 585/352; 585/22
[58] Field of Search ............................ 585/352, 21, 22

[56]  References Cited

U.S. PATENT DOCUMENTS 4,849,565 7/1989 Baum et al. ......................... 585/352
4,918,158 4/1990 Baum et al. ......................... 585/21

Primary Examiner—Anthony McFarlane
Assistant Examiner—Nhat Phan
Attorney, Agent, or Firm—John H. Crowe

[57] ABSTRACT 1,3-Diethynyl-5,7-dimethyladamantane; 1,3,5-triethynyladamantane; 3,3'-diethynyl-1,1'-biadamantane; 1-ethynyldiamantane; 1,4-diethynyldiamantane; 1,6-diethynyldiamantane and 4,9-diethynyldiamantane as new compositions of matter, and a method of forming them in which adamantane; 1,3-dimethyladamatane; 1-hydroxy-3,5-dimethyladamantane; 1,1'-biadamantane and diamantane are each brominated to form a bromo derivative thereof; the bromo derivative is reacted with vinyl bromide in the presence of a Friedel-Crafts catalyst to convert it to its corresponding 2,2-dibromoethyl derivative and the 2,2-dibromoethyl derivative is subjected to dehydrohalogenation to convert it to its final ethynyl form. The 1,3-diethynyl-5,7-dimethyladamantane; 1,3,5-triethynyladamantane; 3,3'-diethynyl-1,1'-biadamantane; 1,4-diethynyldiamantane; 1,6-diethynyldiamantane and 4,9-diethynyldiamantane can be heat cured to form homopolymers having useful commercial properties. 1,3-Diethynyl-5,7-dimethyladamantane; 1,3,5-triethynyladamantane; 1,4-diethynyldiamantane; 1,6-diethynyldiamantane and 4,9-diethynyldiamantane can be polymerized in the presence of a suitable metal or peroxide catalyst.

3 Claims, No Drawings

ETHYNYL ADAMANTANE DERIVATIVES AND METHODS OF POLYMERIZATION THEREOF

The government has rights in this invention pursuant to Contract F33615-85-C-5139 awarded by the Department of the Air Force.

BACKGROUND OF THE INVENTION

This invention relates generally to ethynyl adamantane derivatives as new compositions of matter and to methods of synthesizing and polymerizing these compounds in formulations having useful commercial properties. At present, composite matrix resins, structural adhesives and surface films are used for a number of aerospace structural applications. Presently available materials for such purposes lack adequate stability and suitable physical properties for certain system design applications. Also, there is a need for improved polymers for use as matrices for carbon-carbon systems. For such applications, polymers compatible with carbon fibers which can be pyrolyzed to yield dense, coherent matrices are needed. Another need is for thermally stable polymers with low dielectric constants for electrical insulator usage.

One approach heretofore taken to obtain improved thermally stable polymers for the above-indicated purposes has involved the attachment of acetylene groups to stable organic structures and polymerization of the acetylenic structures by cyclotrimerization or other mechanisms. Stable linking groups have thus been formed without the polymerization of volatile by-products that would result in mechanical imperfections. Stable heterocycles, aromatic polyethers and similar materials have been linked in this manner. Still there has existed a need for significant improvement in such materials for the above-indicated applications. One such improvement was found in a high temperature thermoset resin obtained by the polymerization of 1,3-diethynyladamantane (DEA), as disclosed in U.S. Pat. No. 4,849,565, issued July 18, 1989, and assigned to the assignee of the present application. Curing of the DEA to the resulting polymer, we found, could be accomplished without a catalyst at 210° C. or by using a metal catalyst at 180° C. We further determined that the polymer showed no glass transition prior to the onset of major thermal decomposition in air at 476° C. (by TGA analysis).

SUMMARY OF THE INVENTION

We have now synthesized and polymerized new examples of acetylenic monomers based on the adamantane structure, and some of the new materials show improved thermal stability compared to DEA polymers. These new monomers are 1,3-diethynyl-5,7-dimethyladamantane; 1,3,5-triethynyladamantane; 3,3'-diethynyl-1,1'-biadamantane; 1-ethynyldiamantane; 1,4-diethynyldiamantane; 1,6-diethynyldiamantane and 4,9-diethynyldiamantane.

The aforesaid monomers were prepared in three steps from the corresponding hydrocarbons. Adamantane and 1,3-dimethyladamantane are commercially available. 1,1'-Biadamantane contains two adamantane rings joined at the bridgeheads and was synthesized by the reaction of 1-bromoadamantane with sodium in xylene (see Reinhardt, H.F., *J. Org. Chem.* 1962, 45, 5404). Diamantane was prepared by a literature procedure (Gund, T.M.; Thielecke, W.; Schleyer, P.v.R. *Org. Syn.* 1974, 53, 30) in which norbornadiene was reacted with bis-(triphenylphosphine)cobalt (II) bromide and boron trifluoride to give the dimer "Binor-S" in 84–88% yield. Binor-S was hydrogenated over platinum oxide (96–99% yield) and rearranged in the presence of $AlCl_3$ to give diamantane in 62–72% yield.

The hydrocarbons adamantane, 1,3-dimethyladamantane, 1,1'-biadamantane, and diamantane were brominated to the corresponding mono-, di- or tribromo derivatives. These reactions were sensitive to reaction conditions and catalysts, which affected the rate of reaction, degree of substitution and in some cases, the location of substitution. Reactions were run in neat bromine or with 1,1,2-trichlorotrifluoroethane (available commercially under the trademarked name Freon 113) as a cosolvent at temperatures ranging from $-15°$ C. to reflux. Iron powder, iron powder and water, ferric chloride, boron tribromide, aluminum chloride and aluminum bromide were employed as catalysts depending on the degree of substitution required. The brominated hydrocarbons were used in crude form or purified by crystallization or chromatography.

The bromination products from 1,3-dimethyladamantane, 1,1'-biadmanatane and diadamantane were than reacted with vinyl bromide in the presence of a Friedel-Crafts catalyst to give the corresponding mono-, bis-, or tris(2,2-dibromoethyl) derivatives. This reaction could be conducted in neat vinyl bromide or in solvents such as Freon 113, methylene chloride or other halogenated or non-halogenated hydrocarbons, Catalysts such as ferric chloride, aluminum chloride and aluminum bromide were effective. Vinyl chloride or acetylene is also expected to be useful in place of vinyl bromide.

The Friedel-Crafts adducts of adamantane, 1,3-dimethyladamantane, 1,1'-biadamantane and diamantane were dehydrohalogenated with base to give the corresponding mono-, di- or triethynyl derivatives. Sodium hydroxide, potassium hydroxide or potassium t-butoxide effected dehydrohalogenation in solvents such as dimethyl sulfoxide, N-methyl pyrrolidone, or triethylene glycol at temperatures ranging from room temperature to 180° C. The 2,2-dibromoethyl derivatives could be partially dehydrohalogenated in aqueous sodium hydroxide with or without cosolvents to give the corresponding 2-bromoethenyl derivatives. The 2-bromoethenyl derivatives could then be dehydrohalogenated to the ethynyl derivatives with potassium hydroxide in dimethyl sulfoxide. Representative synthetic procedures for each of the monomers are given below.

A literature route (Stetter, H.; Wulff, C., *Chem. Ber.* 1960, 93, 1366) to 1,3,5-tribromoadamantane gives mixtures containing the mono-, di-, and tetrabromo compounds, with difficult separation problems. A more satisfactory preparation of the tribromide was developed using aluminum bromide and refluxing bromine. Although the product isolated by this method was contaminated with 5% of the tetrabromide, this impurity was unreactive under Friedel-Crafts conditions and thus posed no problems in the purification of the triethynyladamantane. The tribromide reacted in methylene chloride with vinyl bromide in the presence of a catalytic amount of aluminum chloride to give 1,3,5-tris(2,2-dibromoethyl) adamantane. This Friedel-Crafts adduct was dehydrohalogenated with potassium t-butoxide in DMSO to give 1,3,5-triethynyladamantane in 61% yield (based on tribromide).

1,3-Dimethyladamantane is available from methylcyclopentadient dimer, and polyester-based polymers have been prepared from derivatives of this material. See Khardin, A.P.; Radchenko, S.S. *Russ. Chem, Rev.* 1982, 51, 480. The synthesis of 1,3-dibromo-5,7-dimethyladamantane has been reported without experimental detail; Gerzon, K.; Krumkalns, E.V.; Brindle, R.L.; Marchall, F.J. and Root, M.A. *J. Med. Chem.* 1963, 6, 760. We found that the commercially available 1,3-dimethyl-5-adamantanol can be brominated in bromine, in the presence of catalytic amounts of $BBr_3$ and $AlBr_3$, to give 1,3-dibromo-5,7-dimethyladamantane in 76% yield. Since in this derivative, the remaining two bridgehead positions are blocked with methyl groups, no problems were encountered with the formation of polybrominated materials. This dibromo compound was converted to the diethynyl derivatives in 50% yield by the aluminum bromide catalyzer reaction with neat vinyl bromide followed by dehydrohalogenation with potassium t-butoxide in DMSO.

1,1'-Biadamantane, in which two adamantane rings are joined at bridgehead carbons, was brominated to give 3,3'-dibromo-1,1'-biadamantane in 80% yield. Again see Reinhardt H.F. *J. Org. Chem.* 1962, 45, 5405. Reaction of this dibromo compound with aluminum bromide in neat vinyl bromide gave the bis(2,2-dibromoethyl) derivative, which was converted to the corresponding diethynyl derivative in 48% yield by dehydrohalogenation with potassium t-butoxide in DMSO.

The aluminum bromide catalyzed reaction of 1-bromodiamantane (see Gund, T.M.; Schleyer, P.v.R. *Tetrahedron Lett.* 1971, 1583) with vinyl bromide in methylene chloride followed by dehydrohalogenation of the adduct with potassium t-butoxide in DMSO gave a mixture of five components. This mixture was separated by column chromatography and components were identified as diamantane (5%), 1-(2-bromovinyl)-diamantane (8%), 1-ethynyldiamantane (50%), 4-(2-bromovinyl)-9-ethynyldiamantane (9%), and 4,9-diethynyl-diamantane (30%). The formation of 2-bromovinyl compounds results from incomplete dehydrohalogenation, and indicates that the elimination is slower than that observed for the adamantane system. The presence of diamantane and 4,9-diethynyl derivatives indicates the facile disproportionation chemistry in this system. In 1-ethynyldiamantane the ethynyl group is on the girdle, whereas in the case of the 4,9- disubstituted derivative, the ethynyl groups are on the epical positions. Although reaction condition were not found to give pure 1-ethynyldiamantane (similar difficulty was encountered with 1-ethynyladamantane), yields were improved to greater than 55% by the use of ferric chloride as the catalyst and hexane/methylene chloride as the solvent.

A mixture of 1,4- and 4,9-dibromodiamantane was prepared by reacting diamantane with bromine in the presence of aluminum bromide or iron powder. By running the Friedel-Craft reactions in neat vinyl bromide at −50° C., disproportionation was minimized and a mixture of the two diacetylenes was obtained. The mixture was separated by column chromatography to give 26% of the 4,9-isomer and 37% of the 1,4- isomer. The less symmetric 1,4- isomer melted at 83–84° C., whereas the highly symmetric diepical 4,9- isomer melted at 196–198° C. and showed only 3 carbon signals for the ring carbons in the $^{13}C$ NMR spectrum.

A mixture of 1-bromo and 1,6-dibromodiamantane was prepared by a literature procedure as set forth in the above-identified (Gund, T.M.; Thielecke, W.; Schleyer P. v. R. *Org. Syn.* 1974, 53, 30)reference. This material was converted by our standard procedures to a mixture of ethynyl and diethynyldiamantanes. Column chromatography gave a 7% yield of a diethynyldiamantane was a melting point of 168–172° C. This material was identified by $^{13}C$ NMR as the 1,6- isomer, the symmetric derivative disubstituted at the "girdle" positions. This C-18 compound shows 5 carbon signals for the ring carbons in the $^{13}C$ NMR spectrum.

1-Ethynyladamantane undergoes copolymerization with 1,3- diethynyladamantane but does not give a homopolymer. 1-Ethynyldiamantane also was found not to give a homopolymer. The other ethynyladamantanes and diamantanes and biadamantane prepared here underwent thermal polymerization above 200° C. to give clear brown materials with excellent thermal stability. Best results were obtained when the monomers were step cured at temperatures starting at 200° C. and increasing 5–10° C. every 6 hours until the samples were fully cured (230–280° C. and then, reversing the cycle, at b 15° C. an hour to ambient temperature. If the cure cycle was interrupted before gelation, and the monomer was removed by extraction with hexane, oligomeric material could be obtained. Either the monomers or the oligomers could be cured alone or in combinations to give copolymer. Ethynyladamantane monomers have significant volatility at elevated temperatures. Therefore, most samples were cured in sealed glass tubes or in capped molds. No significant pressure develops during the cure, so that minimum containment is required.

1,3,5-Trriethynyladamantane was cured in a sealed tube at 200–230° C. to give a light brown resin. Partially curing the monomer by heating for 16 hours at 201° C. gave 50% conversion to a 1200 molecular weight prepolymer (compared to 210° C. required for the diethynyl derivative.) Extraction of the oligomer with pentane gave an insoluble fraction consisting mainly of high molecular weight materials and a soluble fraction consisting mainly of the pure monomer; no low molecular weight oligomers were obtained. Attempts to cure 1,3,5-triethynyladamantane rapidly or on a large scale lead to an exothermic decomposition. This material could be used in copolymers with other ethynyladamantanes or diamantanes to provide additional cross-linking.

1,3-Diethynyl-5,7-dimethynyladamantane was found to polymerize under conditions similar to those for 1,3-diethynyladamantane and the homopolymers show similar thermal stability to DSC and TGA. No $T_g$ is observed in the DSC over the range 20–450° C. The TGA shows the onset of major decomposition at 466° C.

In 3,3'-diethynyl-1,1'-biadamantane, the acetylene groups are present on separate adamantane rings, and low reactivity similar to that of 1-ethynyladamantane might be expected. However, this material was found to give a thermally stable homopolymer under conditions similar to 1,3-diethynyladamantane with no Tg observed over the range of 20–450° C. and the onset of major decomposition at 471° C. in helium and 477° C. in air.

Diethynyldiadamantanes could be cured to form homopolymers or copolymers with generally higher onsets of major decomposition than the diethynyladamantanes. The lower melting isomer, 1,4-diethynyldiamantane, cured to a homopolymer (onset of exotherm at 519° C.) under the conditions used with 1,3-diethynyladamantane (onset of exotherm 474° C.). Because of the high melting points, the 1,6- and 4,9- isomers were more difficult to cure, but also gave homopolymers (onsets of exotherm greater than 500° C.). Mixtures of the 1,4-, with the 1,6- or the 4,9- isomers with or without the mono substituted material were processed more easily. These monomer mixtures were liquids at room temperature and gave copolymers with properties similar to those of the homopolymers. The copolymers showed no Tg over the range of 20-450° C. and had onsets of major decomposition over 500-520° C.

The ethynyladamantanes and diamantane monomers were also found to undergo metal or peroxide catalyzed polymerization. The most effective catalysts were found to be nickel (II) acetylacetonate and palladium (II) bis(benzonitrile) chloride, but other metal acetylacetonates including those of iron, chromium or molybdenum are also effective. Metal catalyzed polymerization occurs above 180° C.

The following structural formulas illustrate the nature and character of the reactions and compositions embodying this invention.

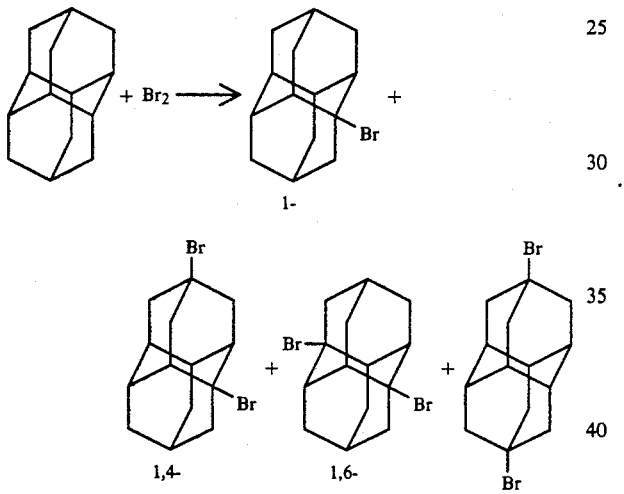

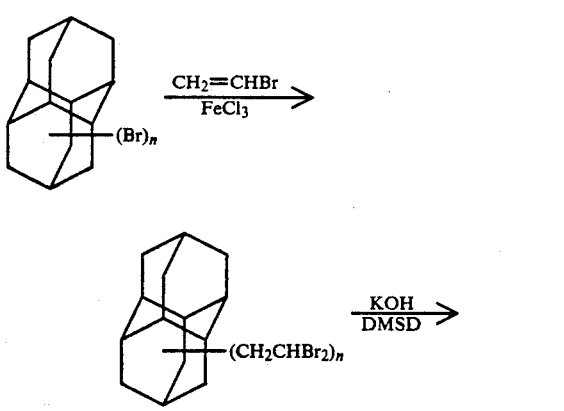

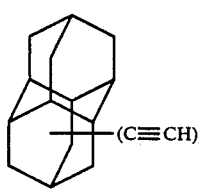

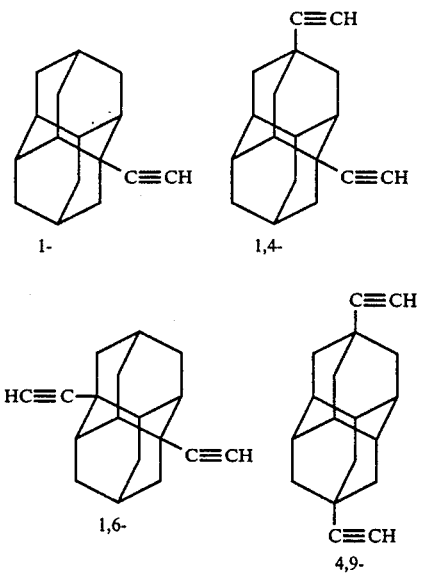

ETHYNYL AND DIETHYNYLDIAMANTANES

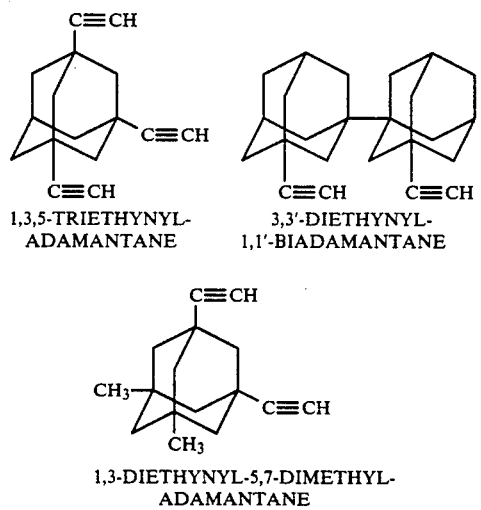

1,3,5-TRIETHYNYL-ADAMANTANE 3,3'-DIETHYNYL-1,1'-BIADAMANTANE 1,3-DIETHYNYL-5,7-DIMETHYL-ADAMANTANE

DESCRIPTION OF THE PREFERRED EMBODIMENTS

Following are examples included to specifically illustrate procedures generally described above. It is to be understood that these examples are offered merely as a means of illustration and are not intended to limit the scope of the invention to any particular combination of materials, conditions, proportions, etc., set forth therein.

EXAMPLE I

Synthesis of 1,3,5-Triethynyladamantane

Vinyl bromide (60 mL) was added, dropwise, over 1.5 h to a solution of 1,3,5-tribromoadamantane (43 g, 115 mmol) and aluminum chloride (10 g) in $CH_2Cl_2$ (100 mL) at a rate such that the internal temperature did not exceed $-20°$ C. The progress of reaction, as indicated by the disappearance of 1,3,5-tribromoadamantane, was monitored by GLC and $^1$H NMR. The reaction mixture was stirred at $-20°$ C. for 1.5 hours, diluted with dichloromethane and poured slowly over crushed ice and concentrated hydrochloric acid (40 mL). The organic layer was separated and the aqueous layer was extracted with dichloromethane. The combined organic layers were washed with water, dried (MgSO$_4$) and filtered and solvent was evaporated under reduced pressure to give 80 g of crude 1,3,5-tris(2,2-dibromoethyl)adamantane.

The crude material was dissolved in DMSO (350 mL) and potassium t-butoxide (80 g, 714 mmol) was added portion-wise over a period of 20 minutes. The mixture was stirred at ambient temperature for 48 h, diluted with dichloromethane and poured over crushed ice/water/concentrated hydrochloric acid (5 mL). The organic layer was separated and the aqueous layer was extracted with dichloromethane. The combined organic layers were washed with water and brine, dired (MgSO$_4$), filtered and stripped of solvent under reduced pressure to give an oil. This oil was distilled under reduced pressure (120-130° C./0.5 mm) to give 14,6 g (61%) of 1,3,5-triethynyladamantane. An analytical sample was recrystallized from pentane: mp. 84-86° C; IR 3350 and 2150 cm$^{-1}$; $^1$H NMR δ 2.13 (s, 3 H, C≡CH) and 1,96 (s, 6 H) and 1.79 (m, 7 H); Anal. Calcd for C$_{16}$H$_{16}$; C, 92.26; H, 7.74. Found: C, 92.10; H, 7.79.

EXAMPLE II

Synthesis of 1,3-Diethynyl-5,7-dimethyladamantane

1-Hydroxy-3,5-dimethyladamantane (4 g, 22.3 mmol) was added, portionwise, over 30 min, to a stirred mixture of boron tribromide (6.6 mL) and aluminum bromide (0.6 g, 2.2 mmol) in bromine (15 mL). The mixture was stirred at room temperature for 29 h, diluted with CH$_2$Cl$_2$ and poured slowly over crushed ice and 10% aqueous sodium carbonate. Sodium sulfite was added to destroy excess bromine and the resulting mixture was extracted with CH$_2$Cl$_2$. The combined layers were washed with water and brine, dried and filtered. Solvent was evaporated under reduced pressure to give 5.8 g of a yellow solid. Recrystallization of this solid from methanol gave 5.4 g (76%) of 1,3-dibromo-5,7-dimethyladamantane: mp 115-116° C.; $^1$H NMR δ2.59 (s, 2 H) 1.92 (s, 8 H), and 0.89 (s, 6 H). Anal. Calcd for C$_{12}$H$_{18}$Br$_2$: C, 44.75; H, 5.63; Br, 49.62. Found: C, 45.00; H, 5.68; Br, 49.74.

Aluminum bromide (0.7 g, 2.6 mmol) was added, portionwise, over 30 min to a solution of 1,3-dibromo-5,7-dimethyladamantane (4.1 g, 13 mmol) in vinyl bromide (35 mL) at a rate such that the internal temperature did not exceed −45° C. The mixture was stirred at −45° C. for 30 mins, diluted with dichloromethane, and poured over crushed ice and concentrated hydrochloric acid (15 mL). The organic layer was separated and the aqueous layer was extracted with dichloromethane. The combined organic layers were washed with water and brine, dried (MgSO$_4$) and filtered. Solvent was evaporated under reduced pressure to give 6.8 g (98%) of crude, 1,3-bis(2,2-dibromoethyl)-5,7-dimethyladamantane: $^1$H NMR δ 5.59 (t, 2 H, J=6 Hz), 2.53 (d, 4 H, J=6 Hz), 1.20 (m, 12 H), and 0.86 (s, 6 H).

The crude adduct (6.8 g) was dissolved in DMSO (35 mL) and potassium t-butoxide (7 g) was added, portionwise, over 15 min. The mixture was stirred at room temperature for 16 h, diluted with dichloromethane, and poured over crushed ice and concentrated hydrochloric acid (20 mL). The organic layer was separated and the aqueous layer was extracted with dichloromethane. The combined organic layers were washed with water and brine, dried (MgSO$_4$) and filtered. Solvent was evaporated under reduced pressure to give 4.5 g of brown oil. This oil was chromatographed over silica gel (85:15 hexane/CH$_2$Cl$_2$) to give 1.4 g (50% based on 1,3-dibromo-5,7-dimethyladamantane) of 1,3-diethynyl-5,7-dimethyladamantane. Analytically pure 1,3-diethynyl-5,7- dimethyladamantane was prepared by short-path distillation: bp 84-85° C./0.1 mm-Hg; TLC (80:20 hexane/CH$_2$Cl$_2$) R$_F$0.51; IR (CDCl$_3$) 3350, 2950, 2150, 1450, 1355 and 1250 cm$^{-1}$; $^1$H NMR δ 2.06 (s, 2 H), 1.79 (s, 2 H), 1.46 (br s, 8 H), 1.1 (s, 2 H), and 0.86 (s, 6 H); Anal. Calcd for C$_{16}$H$_{20}$: C, 90.50; H, 9.50; H, 9.50. Found: C, 90.31; H, 9.60.

EXAMPLE III

Synthesis of 3,3'-Diethynyl-1,1'-biadamantane

Aluminum bromide (1.2 g, 4.5 mmol) was added, portionwise over 30 min, to a solution of 3,3'-dibromo-1,1'-biadamantane (4.0 g, 9.3 mmol) in vinyl bromide (45 mL), at a rate such that the internal temperature did not exceed −25° C. The mixture was then stirred at −30° C. for 45 min, diluted with dichloromethane, and slowly poured over crushed ice and concentrated hydrochloric acid. The organic layer was separated and the aqueous layer was extracted with dichloromethane. The combined layers were washed with water and brine, dired (MgSO$_4$) and filtered. Solvent was evaporated under reduced pressure to give 6.8 g of crude 3,3'-bis-(2,2-dibromoethyl)-1,1'-biadamantane.

The crude product was dissolved in 50 mL of DMSO and potassium t-butoxide (6.3 g, 56 mmol) was added. The mixture was stirred at room temperature for 63 h, diluted with dichloromethane and poured over crushed ice and concentrated hydrochloric acid. The organic layer was separated and the aqueous layer was extracted with dichloromethane. The combined organic extracts were washed with water and brine, dried (MgSO$_4$) and filtered. Solvent was evaporated under reduced pressure to give 3.3 g of a brown viscous oil. This oil was chromatographed over silica gel (75:256 hexane/CH$_2$Cl$_2$) to give 1.35 g (48%) of 3,3'-diethynyl-1,1'-biadamantane: mp 208-210° C.; IR 3350, 2950 and 2150 cm$^{-1}$; $^1$H NMR δ2.03 (s, 2 H, C≡CH), 2,0 (m, 4 H), and 1.49-1.76 (m, 24 H). Anal. Calcd for C$_{24}$H$_{30}$: C, 90.50; H, 9.50. Found: C, 90.20; H, 9.40.

EXAMPLE IV

Synthesis of 1-Ethynyldiamantane

A mixture of 1-bromodiamantane (2 g, 7.5 mmol) and a ferric chloride (0.5 g) in 1:2 hexane/CH$_2$Cl$_2$ (30 mL) was cooled to 0° C. and a solution of vinyl bromide (2 mL, 28 mmol) in hexane (10 mL) was added dropwise over 10 min. The mixture was stirred at 0° C. for 30 min, diluted with dichloromethane, and poured over crushed ice and concentrated hydrochloric acid. The organic layer was separated and the aqueous layer was extracted with dichloromethane. The combined organic extracts were washed with water and brine, dried (MgSO$_4$) and filtered. Solvent was evaporated under reduced pressure to give 2.8 g of an oil. This oil was dissolved in DMSO (50 mL) and potassium t-butoxide (3.5 g, 31 mmol) was added. The mixture was stirred at room temperature for 3 days, diluted with dichloromethane and poured over crushed ice and concentrated hydrochloric acid. The organic layer was separated and the aqueous layer was extracted with dichloromethane. The combined organic extracts were washed with water and brine, dried (MgSO$_4$) and filtered. Solvent was evaporated under reduced pressure to give an oil which was distilled (115° C./0.1 mm) to give 1.0 g of crude 1-ethynyldiamantane as an oil. This oil was chromatographed over silica gel (95:5 hexane/CH$_2$Cl$_2$) to give 0.87 g (55%) of 1-ethynyldiamantane: mp 74–76° C; IR 3350, 2950, and 2150 cm$^{-1}$; $^1$H NMR (CDCl$_3$) δ 2.0 (s, 1 H, C≡CH), and 1.66–1.79 (m, 19 H); Anal. Calcd for C$_{16}$H$_{20}$: C, 90.51; H, 9.49. Found: C, 90.66; H, 9.53.

EXAMPLE V

1-Ethynyl and 4,9-Diethynyldiamantane from 1-Bromodiamantane

A solution of 1-bromodiamantane (3.8 g, 14.2 mmol) and vinyl bromide (5 mL) in CH$_2$Cl$_2$ (25 mL) was cooled with a dry ice-acetone bath (−30° C.). Aluminum bromide (1.3 g, 4.9 mmol) was added, portionwise, over 30 min while the internal temperature was kept below −24° C. The mixture was stirred at −30° C. for 45 min, diluted with dichloromethane and slowly poured over crushed ice and concentrated hydrochloric acid 20 mL). The organic layer was separated and the aqueous layer was extracted with dichloromethane. The combined organic layers were washed with water and brine, dried and filtered. Solvent was evaporated under reduced pressure to give 3.5 g of a colorless viscous oil.

The oil was dissolved in DMSO (50 mL) and potassium t-butoxide (4 g, 36 mmol) was added over 1 h. The mixture was stirred at room temperature for 3 d and then heated at 50–55° C. for 3.5 h. Standard isolation procedure with CH$_2$Cl$_2$ gave 3.5 g of an oil. Bulb-to-bulb distillation of this oil (130° C./0.1 mm) gave 2.6 g of a white semi-solid residue. The residue was chromatographed on silica gel (hexane and 95:5 hexane/CH$_2$Cl$_2$) to give (listed in order of elution): 1-Bromovinyldiamantane: IR (CDCl$_3$) 3150, 2950, 1620, and 1440 cm$^{-1}$; $^1$H NMR δ 5.82 (d, J=3 Hz, 2 H), 1.56–1.69 (m, 19 H).

1-Ethynyldiamantane: mp 74–76° C., identical IR, $^1$H NMR and glc to authentic material.

4-Bromovinyl-9-ethynyldiamantane: mp 128–140° C.; IR (CDCl$_3$) 3350, 2950, 2150, 1630, and 1460 cm$^{-1}$; $^1$H NMR δ 5.82 (d, J=3 Hz, 2H), 2.03 (s, 1 H), and 1.56–1.86 (m, 19 H).

4,9-Diethynyldiamantane: 1.1 g (36%) of ca. 90% pure 4,9-diethynyldiamantane. Analytically pure material was obtained by recrystallization from methanol followed by sublimation: mp 196–198° C.; IR (CDCl$_3$) 3350, 2950, 2150, 1400 and 1360 cm$^{-1}$; $^1$H NMR δ 2.07 (s, 2 H) and 1.83 (br s, 18 H); $^{13}$C NMR (CDCl$_3$) δ 27.4, 36.0, 42.9, 67.1 and 92.2; glc (OV-17, 170 to 270° C. at 16° C./min) R$_T$ 3.0 min.

Anal. Calcd for C$_{18}$H$_{20}$: C, 91.47; H, 8.53. Found: C, 91.60; H, 8.50.

EXAMPLE VI

Synthesis of 1,4- and 4,9-Diethynyldiamantanes from 1,4- and 4,9-Dibromodiamantanes A 3-necked flask fitted with a low temperature thermometer, magnetic stirrer and a nitrogen inlet was charged with a mixture of 1,4- and 4,9-dibromodiamantanes (2.0 g, 5.8 mmol) and vinyl bromide (25 mL). The solution was cooled at −50° C., and aluminum bromide (0.6 g, 2.2 mmol) was added, portionwise, over 30 min, at a rate such that the internal temperature did not exceed −45° C. The progress of the reaction was monitored by $^1$H NMR spectroscopy. The mixture was stirred for 30 min at −50° C., and diluted with dichloromethane and slowly poured over crushed ice and concentrated hydrochloric acid (20 mL). The organic layer was separated and the aqueous layer was extracted with dichloromethane. The combined organic layers were washed with water and brine, dried, and stripped of solvent under reduced pressure to give 6.5 g of a colorless viscous oil.

This oil was dissolved in DMSO (25 mL) and potassium t-butoxide (3.1 g, 28 mmol) was added over 30 mins. The mixture was stirred at room temperature for 3 days, diluted with dichloromethane, and slowly poured over crushed ice and concentrated hydrochloric acid. The organic layer was separated and the aqueous layer was extracted with dichloromethane. The combined layers were washed with water and brine, dried and filtered. Solvent was evaporated under reduced pressure to give 2 g of a brown semi-solid residue. This residue was chromatographed over silica gel (90% hexane/dichloromethane) to give 0.35 g (26%) of 4,9-diethynyldiamantane and 0.5 g (37%) of 1,4-diethynyldiamantane.

1,4-diethynyldiamantane: mp 81–83° C.; TLC (90% hexane/CH$_2$Cl$_2$) R$_F$ 0.31; GC (OV-17, 170 to 290° C. at 16° C./min) R$_T$ 3.2 min; IR (CDCl$_3$) 3350, 2950, 2150, 1450, and 1260 cm$^{-1}$; $^1$H NMR (CDCl$_3$) δ 2.43 (br s, 1 H), 2.30 (br s, 1 H), 2.13 (s, 1 H), 2.13 (s, 1 H), 2,03 (s, 2 H), 1.92 br s, 2 H) and 1.79 (m, 13 H); Anal. Calcd for C$_{18}$H$_{20}$: C, 91.47; H, 8.53. Found: C, 91.65; H, 8.39.

4,9-diethynyldiamantane: mp 196–198° C.; GC (OV-17, 170° C. at 16° C./min) R$^T$ 3 min; IR (CDCl$_3$) 3350, 2950, 2150, 1400, and 1360 cm$^{-1}$; $^1$H NMR (CDCl$_3$) δ 2.03 (s, 2 H), 1.80 (s, 12 H) and 1.71 (s, 6 H); $^{13}$C NMR (CDCl$_3$) δ92.2, 67.1, 42.9, 36.0, and 27.4; Anal. Calcd for C$_{18}$H$_{20}$: C, 91.47; H, 8.53. Found: C, 91.60; H, 8.50.

EXAMPLE VII

1,6-Diethynyldiamantane from 1-Bromo and 1,6-Dibromodiamantane

A mixture (39 g, 113 mmol) of 1-bromodiamantane (ca. 5%) and 1,6-dibromodiamantane was suspended in CH$_2$Cl$_2$ (340 mL) and then cooled with a dry ice-acetone bath (−30° C.). Vinyl bromide (60 mL) was added and then aluminum bromide (5.3 g, 20 mmol) was added over 1.5 h at a rate such that the temperature was maintained below −25° C. The mixture was stirred at −30° C. for 2 h, quenched with water (5 mL), and warmed to 25° C. The organic layer was washed with 10% aqueous HCl, water, dried (MgSO$_4$) and evaporated to give 70.3 g of an oil.

The residual oil was dissolved in DMSO (400 mL) and THF (100 mL) and potassium t-butoxide (58 g, 515 mmol) was added over 1 h. After 3 days the mixture was diluted with water and extracted with CH$_2$Cl$_2$. The organic layers were washed, dried and stripped of solvent to give 29 g of a viscous brown oil. The oil was distilled (130° C./0.2 mm) and the distillate triturated with pentane to give 4.2 g of a mixture of diethynyldiamantanes. This mixture was chromatographed over silica gel (90% hexane/CH$_2$Cl$_2$) to give 1.8 g of 1,6-diethynyldiamantane as a white solid: mp 168–172° C. (sealed tube); $^1$H NMR (CDCl$_3$) δ 2.25 (s, 4 H), 2.19 (s, 2 H, 1.85 (bs, 12 H), 1.55 (s, 2 H); $^{13}$C NMR δ 90.82, 69.57, 44.12, 40.33, 35.52, 25.92. Anal. Calcd for C$_{18}$H$_{20}$:C, 91.47; H, 8.53. Found: C, 91.79, H, 8.44.

EXAMPLE VIII

Polymerization of 1,3,5-Triethynyladamantane

A sample of 1,3,5-triethynyladamantane (142 mg) was sealed in tube and heated at 210° C. for 3 hours, 230° C. for 4 hours and at 250° C. for 8 hours. The tube was cooled to room temperature and opened to give a polymeric resin.

EXAMPLE IX

Polymerizaton of 1,3-Diethynyl-5,7-dimethyladamantane

A sample of 1,3-diethynyl-5,7-dimethyladamantane (560 mg) was sealed in a glass tube and heated at 210° C. for 60 hours, 230° C. for 3 hours, and at 275° C. for 24 hours. The tube was cooled to room temperature and opened to give a clear, brown colored, polymeric resin. This material exhibited a major onset of thermal degradation, in both air and helium, at 467° C.

EXAMPLE X

Polymerization of 3,3'-Diethynyl-1,1'-biadamantane

A sample of 3,3'-diethynyl-1,140 -biadamantane (179 mg) was heated at 200° C. for 16 hours, 210° C. for 2 hours, 225° C. for 5 hours, and at 250° C. for 16 hours. The polymer, a clear brown colored resin, was obtained in 96% yield. The polymer exhibited a major onset of thermal degradation in air at 477° C. and in helium at 47° C.

EXAMPLE XI

Polymerization of 4,9-Diethynyldiamantane

A sample of 4,9-diethynyldiamantane (275 mg) was sealed in a glass tube and heated at 200° C. for 14 hours, and at 250° C. for 48 hours. The tube was cooled to room temperature and opened to give a clear, brownish yellow polymeric resin. This material exhibited a major onset of thermal degradation in air at 526° C. and in helium at 518° C.

EXAMPLE XII

Polymerization of 1,4-Diethynyldiamantane

A sample of 1,4-diethynyldiamantane was sealed in a glass tube and heated at 180° C. for 1 hours, 220° C. for 48 hours, and at 250° C. for 14 hours. The tube was cooled to room temperature and opened to give a clear, yellowish-brown polymeric resin. This material exhibited a major onset of thermal degradation in air at 523° C. and in helium at 519° C.

EXAMPLE XIII

Copolymerization of 1-Ethynyldiamantane with a mixture of 1,4-Diethynyl- and 4,9-Diethynyldiamantanes A mixture (705 mg) of 1-ethynyldiamantane (55% by weight) and 1,4-diethynyl- and 4,9-diethynyldiamantanes (45% by weight) was sealed in a tube and heated at 175° C. for 2 hours, 200° C. for 14 hours, 210° C. for 8 hours, 225° C. for 48 hours, and at 250° C. for 16 hours. The tube was cooled to room temperature and opened to give a brown colored resin. This material exhibited a major onset of thermal degradation in air at 475° C.

As will now be apparent, the reach of the present invention is widespread and numerous examples and embodiments thereof are described herein to reflect this. It should be understood, however, that this subject matter is not to be construed in a limiting, but only in an illustrative, sense and that the scope of the invention is delimited only by the language of the following claims.

We claim:

1. A new compound wherein said compound is selected from the group consisting of 1,3-diethynyl-5,7-dimethyladamantane; 1,3,5-triethynyladamantane; 3,3'-diethynyl-1,1'-biadamantane; 1-ethynyldiamantane; 1,4-diethynyldiamantane; 1,6-diethynyldiamantane and 4,9-diethynyldiamantane.

2. A new compound in accordance with claim 1, wherein said compound is 1,3-diethynyl-5,7-dimethyladamantane.

3. A new compound in accordance with claim 1, wherein said compound is selected form the group consisting of 1,4-diethynyldiamantane; 1,6-diethynyldiamantane and 4,9-diethynyldiamantane.

* * * * *

UNITED STATES PATENT AND TRADEMARK OFFICE
CERTIFICATE OF CORRECTION

PATENT NO. : 5,017,734
DATED : May 21, 1991
INVENTOR(S) : KURT BAUM et al.

It is certified that error appears in the above-identified patent and that said Letters Patent is hereby corrected as shown below:

Title page, item (75), "Sam" should read --San--; and under line 9, insert --[73] Assignee: Fluorochem Inc., Azusa, Calif.---. Column 1, line 5, change "government" to --Government--. Column 2, line 24, "diadamantane" should be --diamantane-- and "than" should read --then--; line 55, change "relfuxing" to --refluxing--; and line 68, change "clopentadient" to --clopentadiene--. Column 3, line 16, "catalyzer" should be --catalyzed--; and line 48, "condition" should read --conditions--. Column 4, line 20, insert --)-- after "C."; line 26, "copolymer" should be --copolymers--; and line 31, "1,3,5-Trriethynyladamantane" should read --1,3,5-Triethynyladamantane--. Column 7, line 16, change "dired" to --dried--; line 19, "14,6" should be --14.6--; and line 23, change "1,96" to --1.96--. Column 8, line 11, cancel "H,9.50;"; line 26, change "dired" to --dried--; line 40, "75:256" should be --75:25--; and line 43, change "2,0" to --2.0--. Column 10, line 2, change "-5020" to -- -50°--; line 17, insert --organic-- before "layers"; line 29, cancel "2.13 (s, 1 H),", second instance, and change "2,03" to --2.03--; line 33, insert --to 270°C.-- after "170°C."; line 37, change "c," to --C.-- before "91.47"; and line 66, change "2H," to --2H),--. Column 11, line 28, cancel "140" and insert in its place --1'--. Column 12, line 5, change "hours" to --hour--; and line 44, substitute --from-- for "form".

Signed and Sealed this

Fourth Day of May, 1993

Attest:

MICHAEL K. KIRK

Attesting Officer

Acting Commissioner of Patents and Trademarks